(12) United States Patent
Kirtley et al.

(10) Patent No.: US 12,733,957 B2
(45) Date of Patent: Sep. 15, 2026

(54) PARTIAL KNEE DENERVATION SYSTEM AND METHOD

(71) Applicants: Robert G. Kirtley, Tallahassee, FL (US); Kimberly Mackey, Tallahassee, FL (US)

(72) Inventors: Robert G. Kirtley, Tallahassee, FL (US); Kimberly Mackey, Tallahassee, FL (US)

( * ) Notice: Subject to any disclaimer, the term of this patent is extended or adjusted under 35 U.S.C. 154(b) by 57 days.

(21) Appl. No.: 19/026,900

(22) Filed: Jan. 17, 2025

(65) Prior Publication Data

US 2026/0207225 A1 Jul. 23, 2026

(51) Int. Cl.

*A61B 17/56* (2006.01)
*A61B 90/00* (2016.01)
*A61B 17/00* (2006.01)

(52) U.S. Cl.

CPC .............. *A61B 17/56* (2013.01); *A61B 90/36* (2016.02); *A61B 90/39* (2016.02); *A61B 2017/00106* (2013.01); *A61B 2017/564* (2013.01); *A61B 2090/378* (2016.02); *A61B 2090/395* (2016.02)

(58) Field of Classification Search

CPC .......... A61B 17/56; A61B 2017/00106; A61B 2017/564; A61B 17/29; A61B 17/02; A61B 17/06066; A61B 17/06; A61B 17/1675; A61B 17/1764; A61B 2017/0268; A61B 17/32; A61B 90/36; A61B 90/39; A61B 2090/378; A61B 2090/395; A61N 1/36071; A61N 1/36021

See application file for complete search history.

(56) References Cited

U.S. PATENT DOCUMENTS

| | | | | |
|---|---|---|---|---|
| 2014/0276539 | A1* | 9/2014 | Allison | A61M 5/00 607/101 |
| 2021/0268271 | A1* | 9/2021 | Bright | A61N 1/06 |
| 2023/0218434 | A1* | 7/2023 | Karnik | A61F 7/12 606/23 |
| 2024/0399100 | A1* | 12/2024 | Dysart | A61K 31/445 |

FOREIGN PATENT DOCUMENTS

| | | | |
|---|---|---|---|
| CN | 221105909 U | * | 6/2024 |

* cited by examiner

*Primary Examiner* — Katherine M Shi
(74) *Attorney, Agent, or Firm* — J. Wiley Horton

(57) ABSTRACT

A system and method for using targeted denervation to treat knee pain. The relevant nerve branches for a particular patient are located using high resolution of ultrasound. Ultrasound is preferred because of its superior resolution and the dynamic nature of its imaging. A nerve blocking agent is preferably applied to each of the targeted branches and the knee joint is tested in order to see if the temporary block relieves the pain. If the pain is relieved by the nerve block(s) then the patient is a suitable candidate for denervation surgery. Each targeted nerve is exposed and transected.

20 Claims, 18 Drawing Sheets

PARTIAL KNEE DENERVATION SYSTEM AND METHOD

CROSS-REFERENCES TO RELATED APPLICATIONS

Not applicable

STATEMENT REGARDING FEDERALLY SPONSORED RESEARCH OR DEVELOPMENT

Not applicable

MICROFICHE APPENDIX

Not applicable

BACKGROUND OF THE INVENTION

1. Field of the Invention

This invention relates to the field of medicine. More specifically, the invention comprises a system and method for treating knee joint pain by confirming the role of pain transmission in specific knee nerve branches, then isolating and transecting those nerve branches when appropriate.

2. Description of the Related Art

Knee osteoarthritis is a common condition among older patients. It tends to increase with advancing age, causing functional limitations that lead to increasing morbidity and mortality. In the early stages, knee osteoarthritis is treated conservatively. Treatment involves physical therapy, weight management, activity modification, and over-the-counter analgesics. Interventional pain management options include injection-based corticosteroids, viscosupplementation treatments (injecting a natural lubricant such as hyaluronic acid into the knee joint), and genicular nerve radiofrequency ablation (GnRFA).

These interventional techniques can be effective, but only over a limited period of time. Corticosteroid and viscosupplementation often provide relief for a few weeks. GnRFA provides longer relief, but even this approach is only shown to be helpful for 6 to 12 months. Peripheral nerve regrowth and regeneration often occurs following GnRFA treatments and these phenomena cause the knee pain to return. Thus, the known interventional techniques must often be repeated periodically, which can be cumbersome and costly for patients.

The definitive management for terminal knee osteoarthritis is total knee arthroplasty (TKA). TKA is the most commonly performed total joint replacement surgery, with over 600,000 procedures performed each year in the United States. The prevalence for TKA increases with age—reaching 10.38% for TKA by age 80. While the results for TKA are generally good, it is a significant surgery requiring intensive rehabilitation. The TKA patient must be committed to enduring a long and painful process to optimize recovery and regain good knee function. Many candidate patients are unwilling to invest the time needed for proper rehabilitation. TKA also carries risk for significant morbidity and mortality, and while the surgery has a very favorable safety profile for optimized patients, a considerable portion of the general patient population are not suitable candidates for the procedure.

Even where total knee arthroplasty is performed successfully, it does not always eliminate knee pain. The TKA procedure itself can cause nerve injury leading to chronic pain. A common complication for TKA is injury to the infrapatellar branch of the saphenous nerve (the "ISN"). A 2014 study by T. Ackman noted that ISN injury after TKA has an incidence as high as 70%. Multiple studies have shown that cryoablation, radiofrequency ablation, nerve hydrodissections, steroid and other treatment alternatives that do help—but often only temporarily.

The present invention uses joint denervation to provide long-term relief of knee pain. Joint denervation has a well-documented history of long-term pain relief. Partial denervation to the knee joint can alleviate knee pain with a smaller and less invasive procedure than other approaches such as TKA. In order to understand the details of the inventive procedure, it is important to have a basic understanding of the human anatomy involved. Explaining the relevant anatomy is somewhat challenging, as the prior art literature is inconsistent. It is inconsistent both in terms of the nomenclature employed and the anatomy described. For this reason, the inventors act as their own lexicographers in this disclosure. The terms used by the inventors are not novel, but they do eliminate the ambiguity found in prior art descriptions so that a reader has a clear understanding of the anatomy involved and the procedures described and claimed.

Many prior art publications divide the knee into anterior and posterior compartments, and then further divide the anterior compartment into four quadrants. FIG. 1 provides a simplistic anterior depiction of the right knee. Patella 10 lies in the middle of the view. Lateral joint line 12 and medial joint line 14 lie on either side of the patella. The four quadrants of the anterior knee are then superior lateral region 16, superior medial region 18, inferior lateral region 20, and inferior medial region 22. Nerves found in the knee are commonly called "genicular" nerves—the term "genicular" meaning "of or relating to the knee." Many prior medical publication name the genicular nerves according to their location. Using this convention results in the nerves of the knee being named the superolateral genicular nerve (SLGN), the superomedial genicular nerve (SMGN), the inferolateral genicular nerve (ILGN), and the inferomedial genicular nerve (IMGN)—each of which primarily resides in the respective quadrant. The reader will note that this convention provides no information as to the origin of each nerve.

Other prior publications name the nerves using a combination of nerve origin, nerve branching, and anatomical location. The inventors use this approach. In speaking of the nerves of the knee, however, the reader should be aware that considerable anatomical variation exists from individual to individual. Therefore, in trying to create a consistent nomenclature for the nerves of the knee the lexicographer is faced with (a) multiple prior art names for the same nerve branch in the literature, and (b) some uncertainty as to whether the same nerve branch is in fact the same nerve branch given the substantial anatomical variety from patient to patient. The present invention works around these ambiguities by following a process of tracing the relevant nerves from known reference points—as will be described in detail in the disclosure to follow.

The present inventive method considers four particular nerves. These are referred to as:

(1) The infrapatellar saphenous nerve ("ISN");

(2) The medial saphenous nerve ("MSN");

(3) The medial retinacular nerve ("MRN"); and (4) The medial femoral cutaneous nerve ("MFCN").

The ISN is a branch of the saphenous nerve formed from the L3 and L4 nerve roots. It is purely sensory in function and supplies the infrapatellar skin as well as the anterior inferior knee capsule. The location of the ISN varies significantly from patient to patient-which presents a challenge for the present inventive method. The various configurations known for the ISN are normally described with regard to the location of the ISN in a particular patient relative to the sartorius muscle. FIG. 2 provides a very simplistic view of the sartorius muscle and its location relative to other significant anatomical features. The view is an anterior view of a patient's right thigh. The upper end of sartorius muscle 24 connects to anterior superior iliac spine 26. The sartorius muscle wraps helically around the front of the thigh and passes behind adductor tubercle 34 of femur 28. The lower end of the sartorius muscle is attached to the tibia by the sartorius tendon (not shown in FIG. 1).

There are of course many other muscles and structures present in the thigh. For the present purpose, however, only adductor longus muscle 30 is illustrated in FIG. 2 in addition to the sartorius muscle. The upper portion of the adductor longus muscle attaches to pubic tubercle 38. The lower portion of the adductor longus muscle attaches to femur 28. Adductor canal 36 is formed between sartorius muscle 24 and adductor longus muscle 30. This canal forms a passage for nerves and blood vessels. Femoral artery 32 is shown passing through the canal. The saphenous nerve, which is of particular interest in the present invention, also passes through the canal.

The ISN splits from the saphenous nerve proper at the level of medial femoral condyle 40. From that point the saphenous nerve continues distally to the ankle as the distal saphenous branch that supplies the skin of the anterior, medial lower leg and medial ankle. The ISN itself demonstrates four primary anatomical variants. Older anatomical studies found the ISN to be anterior to the sartorius muscle in 27% of cadaver's studied, posterior of the sartorius muscle in 23%, penetrating the sartorius muscle in 37%, and emerging distal to the sartorius muscle's insertion on the pes anserine in 13% (The pens anserine is the region where the tendons of the sartorius, gracilis, and semitendinosus muscles join and attach to the tibia). More recent studies have confirmed these four variants but also found the posterior of the sartorius muscle variant to be the most common at 57%.

The ISN shows even further variation in its distal path. Its branches take four additional possible paths across the patellar tendon. In a cadaver dissection of 60 specimens only one had no ISN branch running through the area between the apex of the patella and tibial tubercle. In the same study, 15 of 60 had one branch, 37 of 60 had two branches, 6 of 60 had three branches and 1 of 60 had four branches. These studies demonstrated the marked variability of the ISN and its terminal branches. This explains why the ISN branches are commonly injured in TKA, arthroscopy, and the harvesting of a tendon for ACL reconstruction.

The second nerve of interest in the present inventive method is the medial saphenous nerve (MSN) which has the same origins of the previously described ISN and is found exiting the sartorius muscle in the mid-thigh. The MSN may contain branches from the saphenous or the medial retinacular nerves, but is consistently seen on ultrasound imaging exiting from the superficial tissues of the sartorius muscle at the mid-thigh level.

The third nerve of interest is the medial retinacular nerve (MRN). The MRN is also often found with visible branches near the medial joint line and is often a target for the inventive procedure if clearly visualized on ultrasound. The MRN is an afferent branch of the femoral nerve and innervates the medial knee joint capsule. According to A. Lee Dellon's book Joint Denervation, the MRN provides sensory input from beneath the patella, from the medial ligaments and from the medial meniscus.

The fourth nerve of interest is the medial femoral cutaneous nerve (MFCN). The MFCN is a branch of the femoral nerve that supplies sensation to the patellar skin. It mirrors the course of the ISN and shows very similar anatomical variability. The MFCN is seen superficial to the sartorius muscle in 39%. It penetrates the sartorius muscle in 30% and it exits deep to the sartorius muscle in 31% (All numbers are from Dellon's book, Joint Denervation).

Additional drawing figures will aid the reader's understanding of the possible locations of the relevant anatomy. The present invention identifies the nerves targeted for treatment at least in part on the basis of the muscle within which the nerve travels. Hence, a basic understanding of the musculature is important.

FIG. 3 provides a view of the thigh with the musculature in place. Sartorius muscle 24 runs from anterior superior iliac spine 26 to sartorius ligament 25 (which connects to the tibia). The sartorius muscle wraps over the front of the thigh. Vastus medialis muscle 42 is one of the four muscles of the quadriceps group. Its upper portion lies beneath the sartorius muscle. FIG. 3 also shows the location of patella 10 and the upper portion of patellar ligament 11—allowing the reader to visualize the location of the sartorius and vastus medialis muscles with respect to the knee.

FIG. 4 is a view of the same area after partial dissection. The sartorius muscle is cut to more fully reveal the location of vastus medialis 24. The knee joint has been partially opened to reveal the joint line between the tibia 94 and the femur 28. The sartorius ligament 25 can be more readily visualized as it passes around the medial femoral condyle 40 and attaches to the tibia 94.

FIGS. 5A and 5B provide a depiction of the distribution of the nerves through the thigh and knee area. FIG. 5A shows the area with the covering musculature removed to reveal internal structures. FIG. 5B shows the same area with the cutaneous nerve branches being visible over the underlying structures. In looking at these figures, the reader should remember the substantial anatomical variation for these nerve distributions from patient to patient. The locations shown are common but by no means certain for a particular patient.

Two of the nerves of interest are shown in FIGS. 5A and 5B. These are the infrapatellar saphenous nerve 46 and the anterior branches 50 of femoral nerve 48—including medial femoral cutaneous nerve ("MFCN") 52.

Saphenous nerve 44 lies beneath sartorius muscle 24 but ultimately passes outward through the sartorius muscle-often in the vicinity of sartorius ligament 25. Infrapatellar saphenous nerve 46 branches off of saphenous nerve 44 at a point superior to the point where the saphenous nerve proper emerges from the sartorius ligament.

As shown in FIG. 5B, the anterior branches of the femoral nerve 50 pass outside the musculature and provide cutaneous innervation. Some of these branches comprise medial femoral cutaneous nerve 52—which can extend inferiorly into the knee joint.

FIG. 6 graphically depicts the distribution of nerves proximate articular knee capsule 54, with the musculature and other structures removed. Saphenous nerve 44 descends along the medial side of the knee as explained previously.

Infrapatellar saphenous nerve 46 branches from the saphenous nerve proper at a point superior to the knee capsule. Additional nerves are present as well, and these are important to consider in carrying out the inventive method.

Medial retinacular nerve 54 often lies superior and medial to the knee capsule. It is generally branched from the tibial nerve or possibly the sciatic nerve itself if the branch occurs in a more superior position. Lateral retinacular nerve 56 often lies superior and lateral to the knee capsule. It is generally branched form the common fibular nerve (peroneal nerve). Recurrent fibular nerve 58 lies inferior and lateral to the knee capsule.

As stated previously, the nerve distributions within the knee vary significantly from one individual to the next. This fact, along with the lack of consistency in the nomenclature used for the nerves of the knee, makes the identification and isolation of the relevant nerves difficult. The present invention overcomes these concerns, as the following descriptive sections demonstrate.

BRIEF SUMMARY OF THE PRESENT INVENTION

The present invention comprises a system and method for using targeted denervation to treat knee pain. The use of high resolution ultrasound to identify the relevant nerve branches for a particular patient is an important advantage of the inventive process and is the preferred embodiment. Nerves demonstrate a slightly brighter appearance on ultrasound referred to as hyperechogenicity; in short, the nerve is a hyperechoic structure. Nerves having a brighter appearance are hyperechoic. The hyperechoic nerves are identified as they exit the sartorius muscle and travel to and around the knee joint.

A nerve blocking agent is preferably applied to each of the targeted branches and the knee joint is tested in order to see if the temporary block relieves the pain. If the pain is relieved by the nerve block(s) then the patient is a suitable candidate for denervation surgery. During surgery, each targeted nerve is marked visually (such as by using a blue dye, methylene blue). Each targeted nerve is also physically separated from the surrounding tissue-such as by hooking the nerve with a spinal needle. These steps provide easy identification when the target nerve is exposed for transection.

REFERENCE NUMERALS IN THE DRAWINGS

Figure 1:
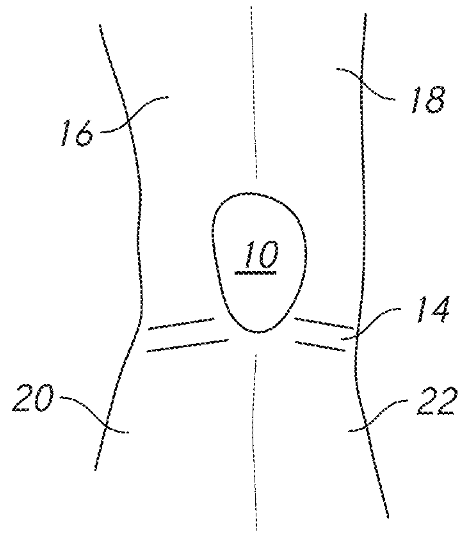
FIG. 1 is an elevation view, showing the anterior regions of the knee.
Figure 2:
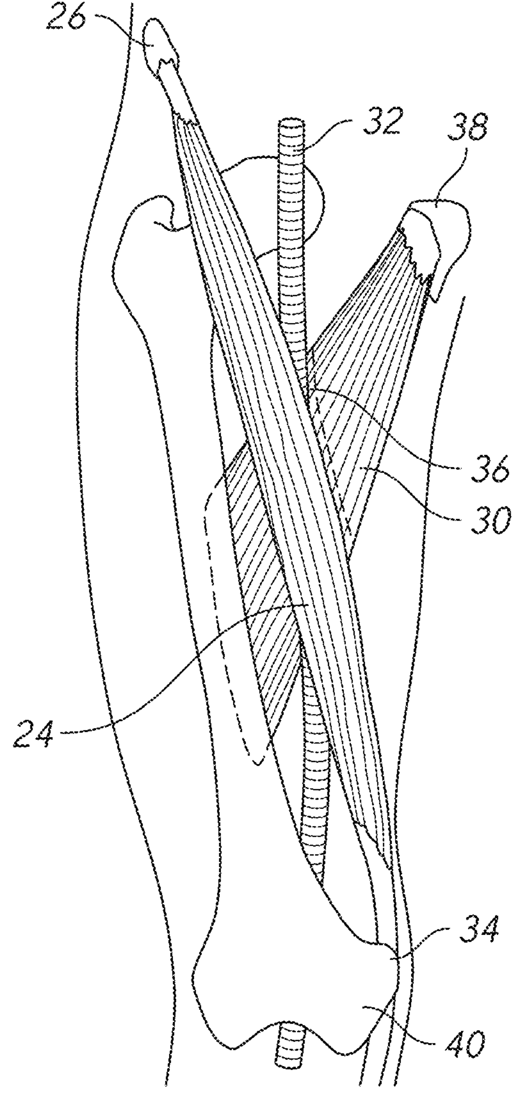
FIG. 2 is an elevation view, showing the internal structure of the thigh.

10 patella
11 patellar ligament
12 lateral joint line
14 medial joint line
16 superior lateral quadrant
18 superior medial quadrant
20 inferior lateral quadrant
22 inferior medial quadrant
24 sartorius muscle
25 distal sartorius tendon
26 anterior superior iliac spine
28 femur
30 adductor longus muscle
32 femoral artery
34 adductor tubercle
36 adductor canal
38 pubic tubercle
40 medial femoral condyle
42 vastus medialis muscle
44 saphenous nerve
46 infrapatellar saphenous nerve
48 femoral nerve
50 anterior cutaneous femoral nerve branches
52 medial femoral cutaneous nerve
54 medial retinacular nerve
55 articular knee capsule
56 lateral retinacular nerve
58 recurrent fibular nerve
60 patient
62 probe
64 ultrasound machine
66 display
68 medial saphenous branch
70 needle
72 dye
74 bent needle
76 stylet
77 depth stop
78 offset
80 epidermis
82 insertion point
84 self retaining retractor
86 incision
88 right angle hemostatic forceps

90 Metzenbaum scissors
92 transected nerve
94 tibia
96 distal third emergence position
98 mid thigh emergence position
100 proximal third emergence position
102 distal third scanning line
104 mid thigh scanning line
106 proximal third scanning line

DETAILED DESCRIPTION OF THE INVENTION

The inventive process begins by identifying suitable candidates for potential denervation. Anyone with chronic knee pain associated with osteoarthritis, degenerative joint disease, post-surgical changes, or trauma is a candidate. Most knee joint pain is associated with loss of joint space in the medial compartment and the inventive procedure works well for those patients. On the other hand, the procedure does not work well for patients with exclusive lateral joint line pain so those patients are excluded.

Once a candidate patient is identified, the targeted nerves must be located. Fluoroscopy has been used in the past for regional guidance, but this is not exact and it is unable to actually visualize the nerve. Fluoroscopy, computed tomography, magnetic resonance imaging and any other imaging modalities other than ultrasound are not capable of adequately imaging the nerve. Ultrasound technology allows for dynamic visualization of the nerve tissue and it is therefore the preferred technology.

Figure 7:
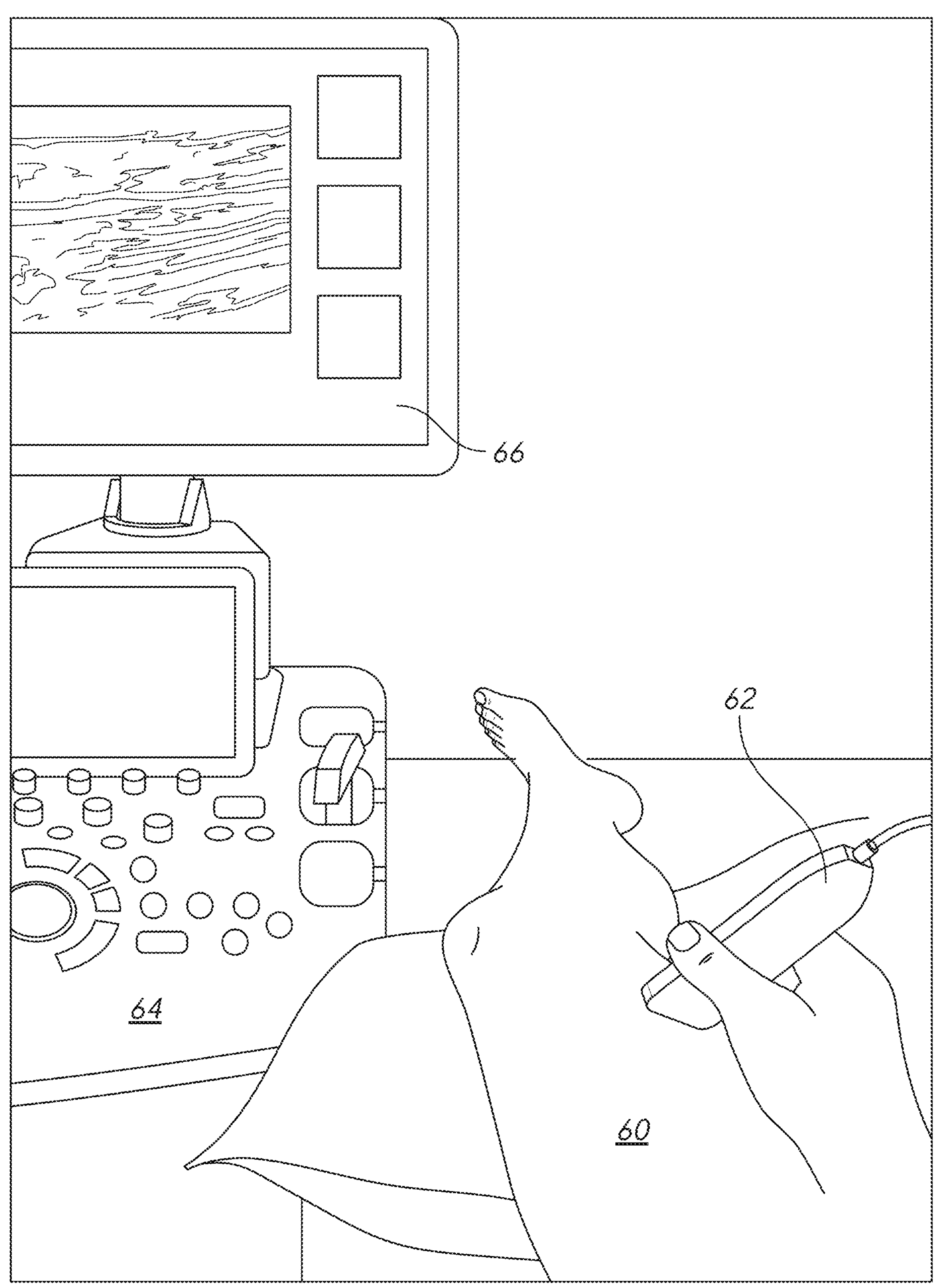
FIG. 7 is a perspective view, showing the use of ultrasound to locate the target nerves.

FIG. 7 shows the use of ultrasound imaging. Patient 60 is placed in a supine position. The proposed operative leg is placed in the frog leg position. Ultrasound machine 64 includes a handheld probe 62 and display 66. The operator moves the probe while monitoring the image provided on the display.

Figure 3:
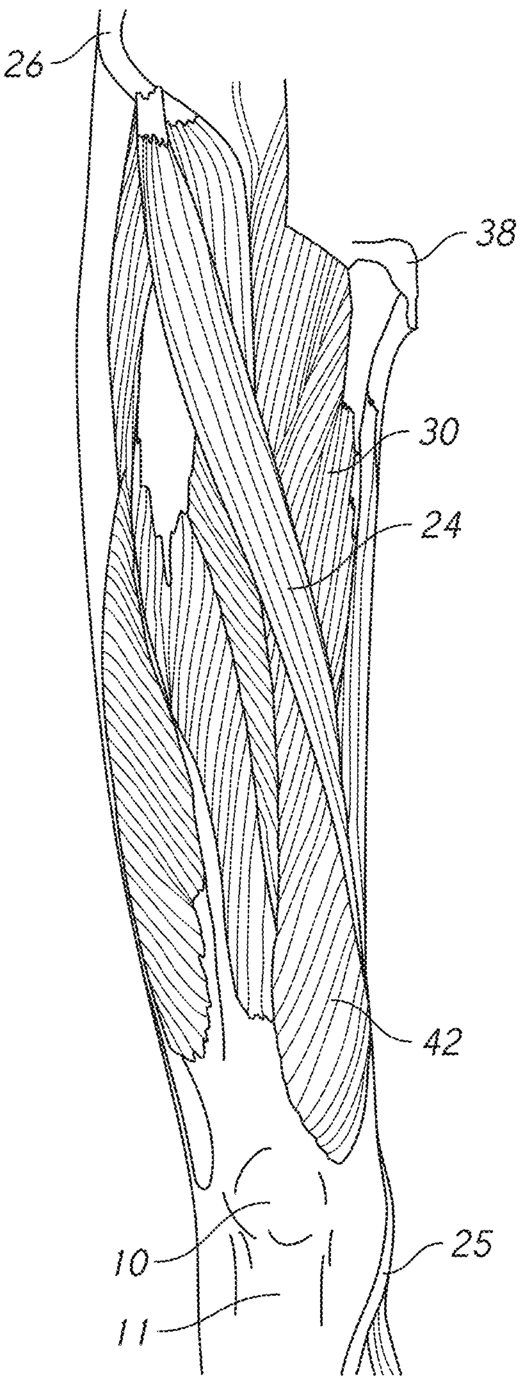
FIG. 3 is an elevation view, showing the intact musculature of the thigh.

The operator starts at the mid-thigh, paying close attention to the sartorius muscle (element 24 shown in FIG. 3). The operator moves the probe while watching for hyper-echoic (bright appearing) round structures that indicate the emergence of a nerve branch from the sartorius muscle. The first emergence is usually found superior to the knee at the mid-thigh. This first emergence is the MSN. Once identified at the point of emergence from the sartorius muscle, this nerve branch can be followed distally (generally downward and toward the knee in terms of a patient's standing orientation) by ultrasound imaging into the medial knee joint. The fibers and branches can be observed as the distribution continues around the knee and into the joint capsule.

Figure 17:
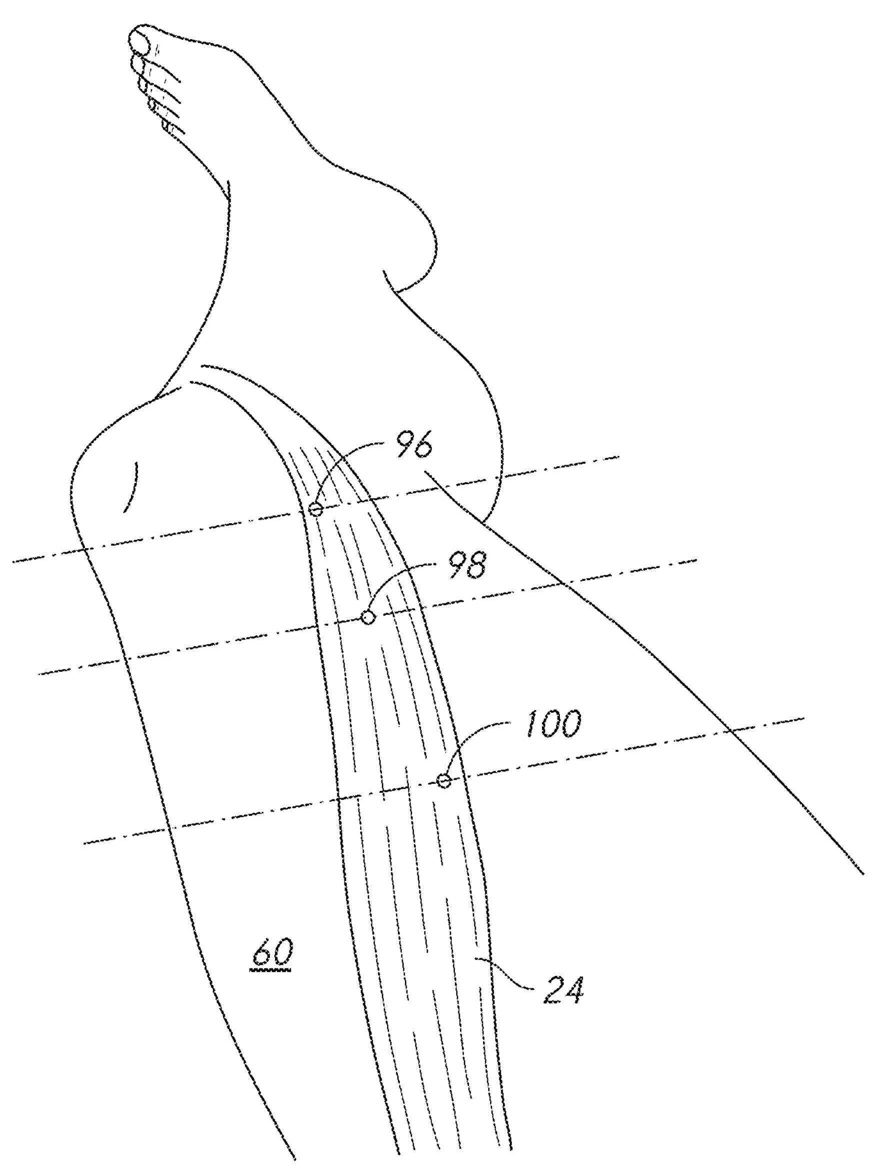
FIG. 17 is a perspective view, showing the common locations where the MSN emerges from the sartorius muscle.
Figure 18:
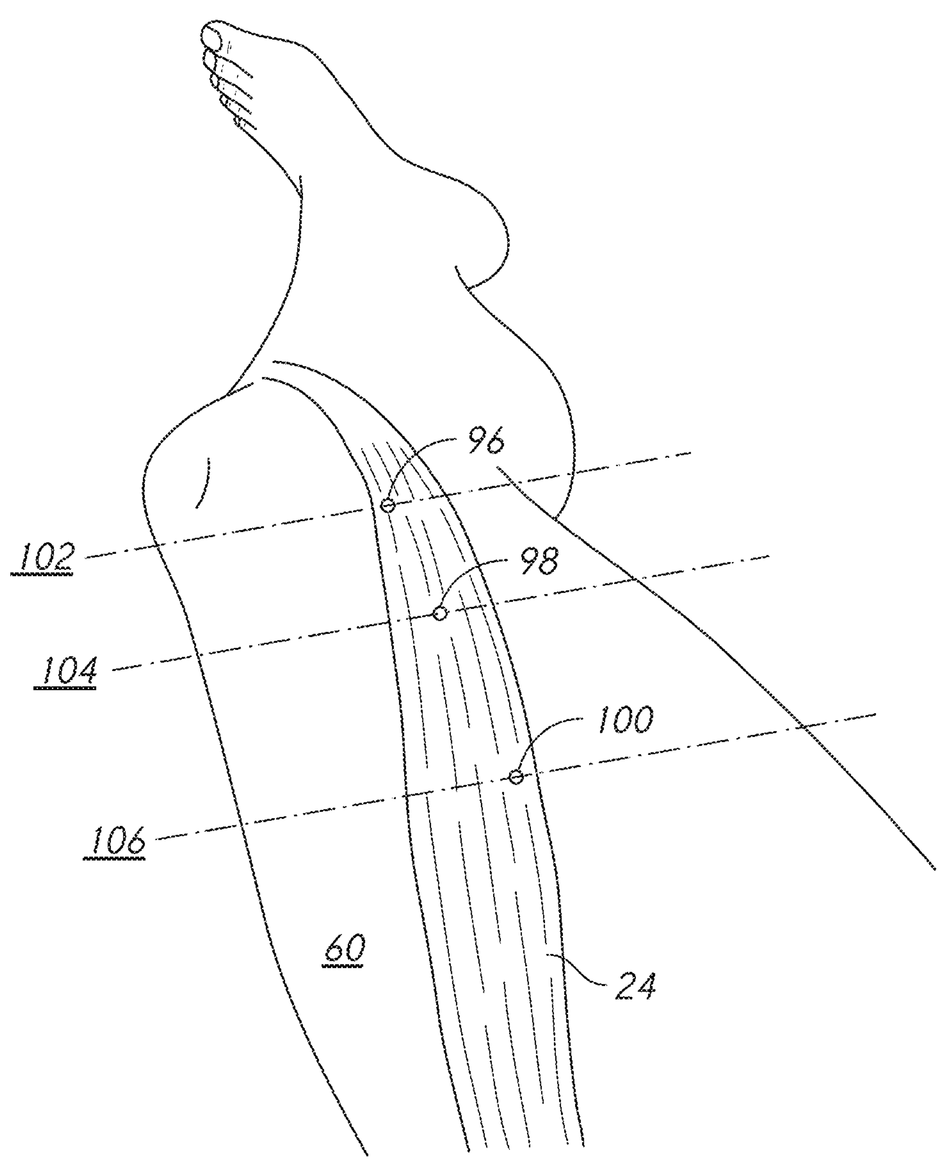
FIG. 18 is a perspective view, showing the preferred ultrasound scanning lined used to locate the position where the MSN emerges from the sartorius muscle.

FIGS. 17 and 18 illustrate the scanning methodology used to locate the first emergence of the MSN from the sartorius muscle. FIG. 17 illustrates the three most common emergence locations. Proximal third emergence position 100 occurs in the proximal third of the sartorius muscle 24. Mid thigh emergence position 98 occurs in the middle of the thigh. Distal third emergence position 96 occurs further down. FIG. 18 illustrates the ultrasound scanning lines of probe travel used to locate these emergence positions. Proximal third scanning line 106 travels lateral-to-medial as shown. Mid thigh scanning line 104 and distal third scanning line 102 also travel lateral-to-medial. The direction of travel is not critical and the scans can be conducted medial-to-lateral as well.

Once the most superior emergence from the sartorius muscle is found the operator should return to the sartorius muscle and continue to detect any additional branches that emerge from the sartorius muscle in a more inferior position. This is another area where considerable patient-to-patient anatomical variations exist. Additional branches may not be present for a particular patient but this region of the sartorius muscle must be carefully scanned to identify any branches that are present.

Figure 4:
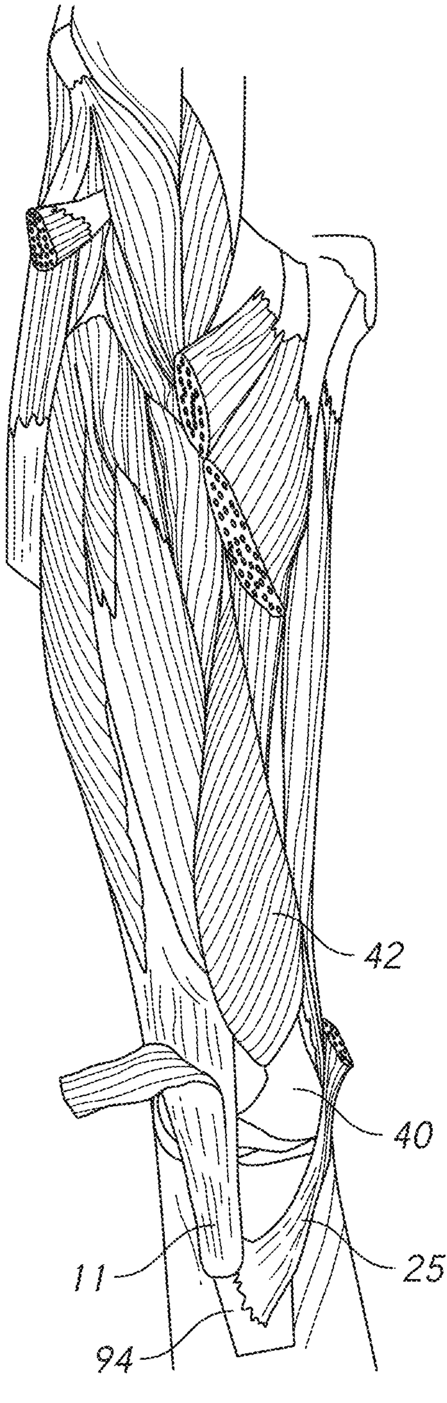
FIG. 4 is an elevation view, showing the partially dissected musculature of the thigh.
Figure 5A:
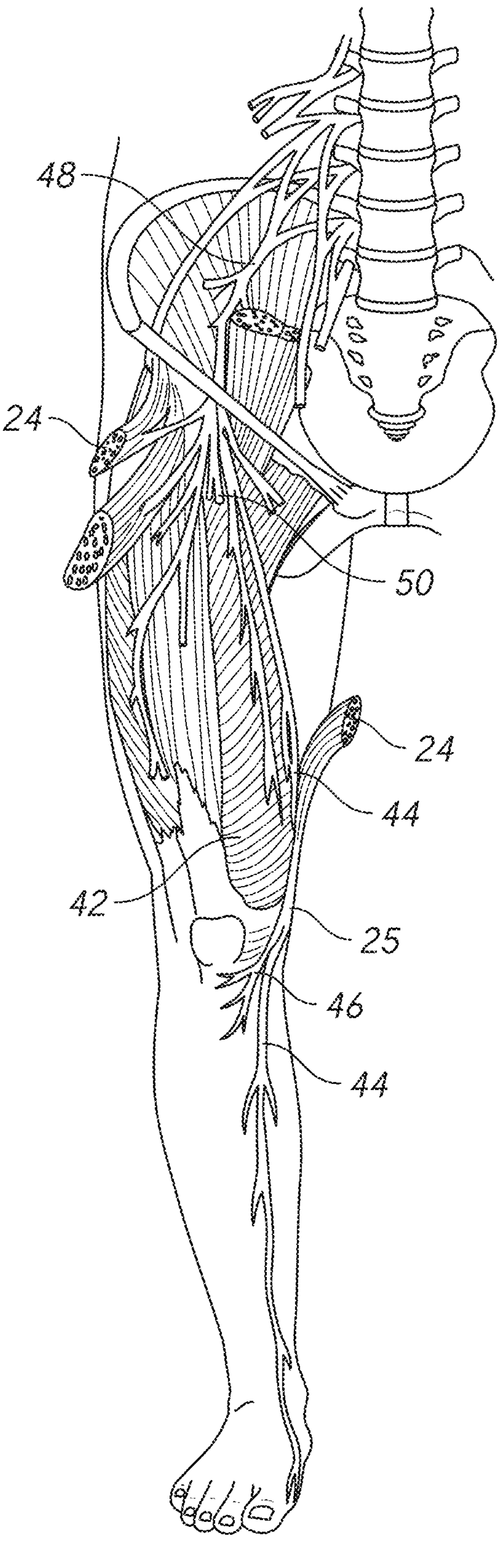
FIG. 5A is an elevation view, showing the internal structures of the pelvis, thigh, and knee.
Figure 5B:
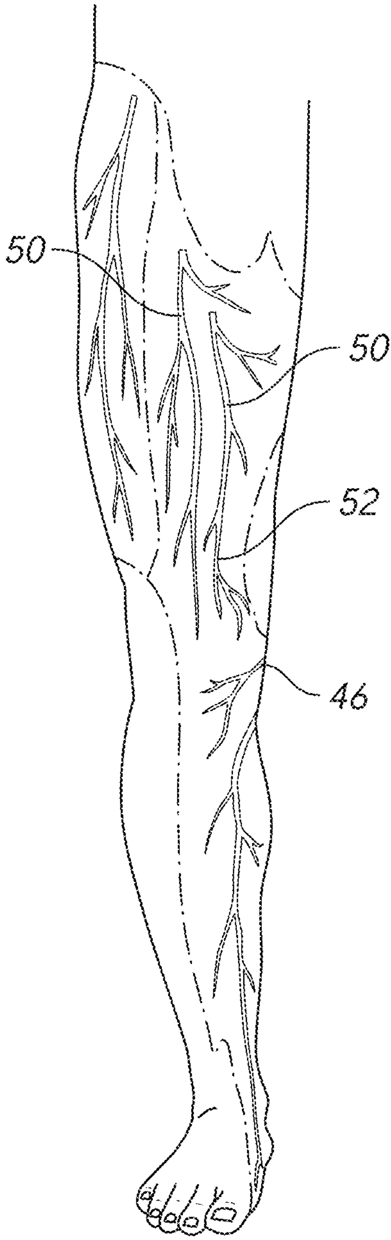
FIG. 5B is an elevation view, showing the distribution of the femoral cutaneous nerves.
Figure 6:
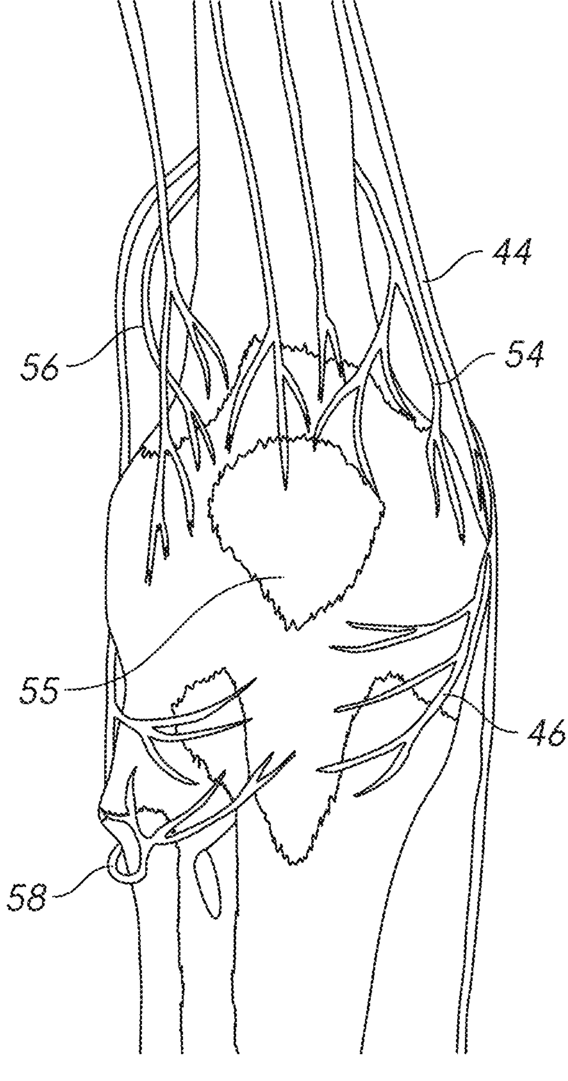
FIG. 6 is a detailed elevation view, showing the distribution of nerve branches around the articular knee capsule.

Finally, in most cases the extremely important ISN (infrapatellar saphenous nerve) can be detected where it emerges from the distal sartorius tendon (element 25 in FIG. 4). The ISN branch of the saphenous nerve either exits through the substance of the distal sartorius tendon and then rapidly curves to the inferior patella region and normally requires 90 degrees of axial rotation of the ultrasound probe in order to visualize this branch. Alternatively, the ISN may exit from some other location around the distal sartorius tendon. The location of each nerve branch found using ultrasound imagery is carefully marked using a small plastic 18-gauge needle cover to make a skin indentation. This can be performed despite the field being covered with ultrasound gel, where a skin marker is difficult to use.

Figure 8:
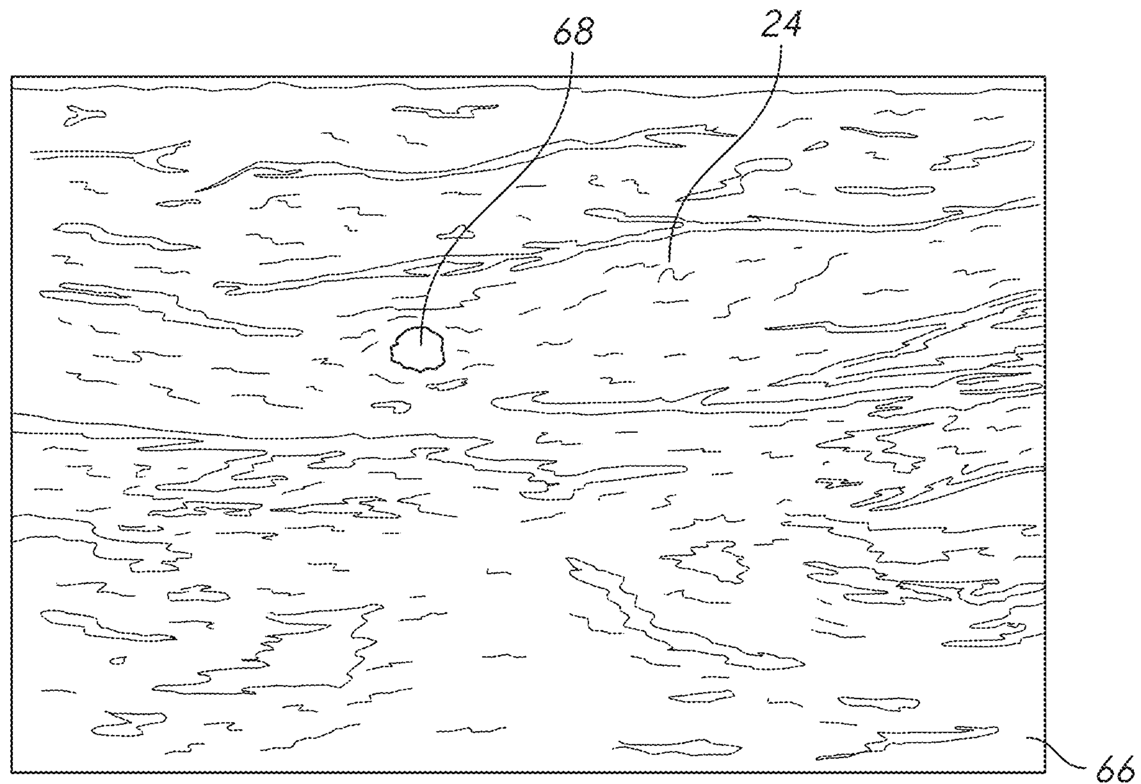
FIG. 8 is an ultrasound image, showing a target nerve.

FIG. 8 is a depiction of an ultrasound view corresponding to the emergence of a nerve branch from the sartorius muscle. The reader will appreciate that a line drawing suitable for reproduction in a patent application is ill suited to the accurate depiction of an ultrasound image, which will ordinarily include many subtle gradations of gray. Nevertheless, FIG. 8 does serve to illustrate how the nerve in question can be distinguished from the surrounding structures if the user is looking in the right anatomical region. The striated appearance of the sartorius muscle itself is shown. Medial saphenous nerve 68 is the circular object depicted-which is in fact a cross section of the nerve branch at that point. This image is from a larger body habitus patient.

Figure 9:
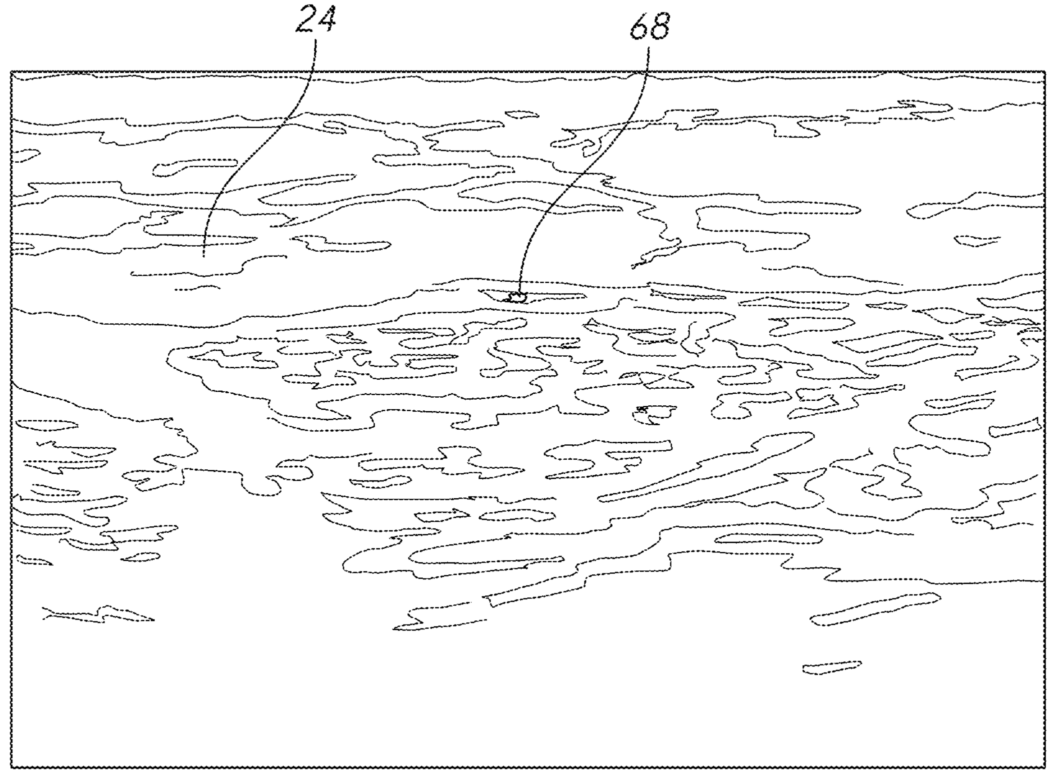
FIG. 9 is an ultrasound image, showing a target nerve.

FIG. 9 shows a comparable nerve branch emergence for a patient with low adiposity. The reader will note how the circular structure at the point of emergence is more difficult to visualize due to the lack of fat surrounding the nerve. The visual appearance on the ultrasound will be different from patient to patient. This is why it is important to identify the anatomical region of emergence from the sartorius muscle and then trace the nerve distribution distally from there.

Pre-Operative Test Procedure

A pre-operative test procedure is performed to ensure that all the relevant nerves have been located. Again using ultrasound guidance, a physician injects a low volume anesthetic (such as <0.5 ml of 0.5% ropivacaine) into each targeted nerve location. The blocks should be administered in the same site where surgical transection is proposed.

After a 5-minute wait for the administered anesthetic to take effect, the knee joint is tested to determine the efficacy of the nerve blocks. The patient is asked to test the joint by bending the knee in a full range of motion (flexion and extension multiple times). If no pain is felt then the patient is asked to perform a two minute test walk. If the patient reports pain relief in the affected knee (preferably >80% pain relief to be a suitable candidate) then he or she is considered a candidate for the inventive denervation surgery. An anatomical description of the nerve patterns is created in clinical notes at the time of the block if it was successful and the patient is deemed a candidate for the denervation procedure.

Denervation Surgical Procedure

The denervation surgery can be performed immediately after a successful pre-operative test procedure, or it may be performed at a later time. The following provides an exemplary sequence:

Step 1—The patient is placed supine on a bed, with the operative leg in frog leg position. The patient is given prophylactic antibiotics.

Step 2—The patient is placed under monitored anesthesia care. This is typically a propofol infusion monitored by an anesthesiologist.

Step 3—The physician reviews the previously blocked nerve locations and the description of the nerve distribution patterns in the clinical notes obtained during the initial clinic visit when the testing block was administered.

Step 4—Looking again at FIG. 7, the physician or operator scans the operative knee using the ultrasound probe 62 in order to find the previously blocked nerves and the best location for surgical transection. These locations are marked on the patient's skin via the previously described indentation method. An indentation marks the location of a nerve directly below the skin and fatty tissue. These indentations serve as reference points for the next steps.

Figure 10:
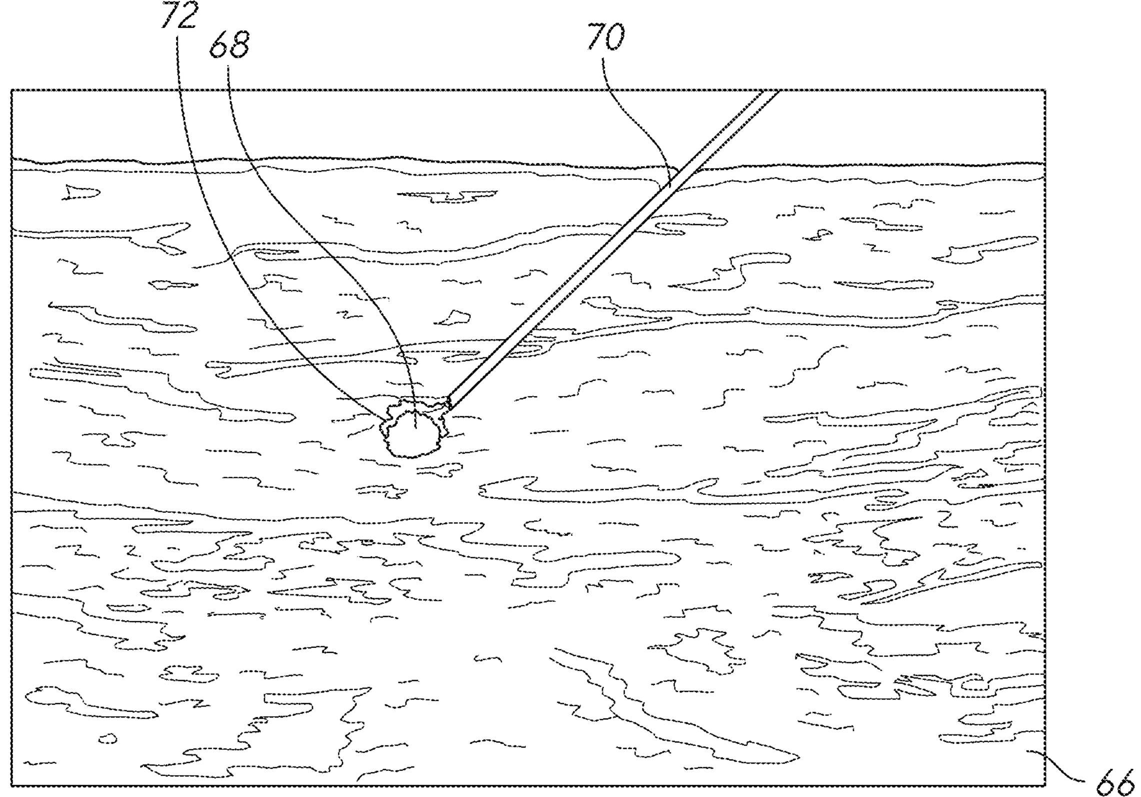
FIG. 10 is an elevation view, showing the injection of a marking dye proximate a target nerve.

Step 5—A marking dye is injected around the nerve proximate the previously-established blocking location. FIG. 10 provides an elevation view of this process. Needle 70 is advanced toward a target nerve—in this case medial saphenous nerve 68. Ultrasound imagery is used to guide the needle tip to the desired location. Dye 72 is then administered around the nerve. The preferred dye is 0.1 to 0.2 ml of methylene blue (tetramethyl thionine chloride, $C_{16}H_{18}ClN_3S$). Methylene blue has a high affinity for nervous tissue and bonds indiscriminately to motor, sensory, and autonomous nerve fibers. It has a long history of safe clinical use. This step is repeated for each target location.

Figure 11:
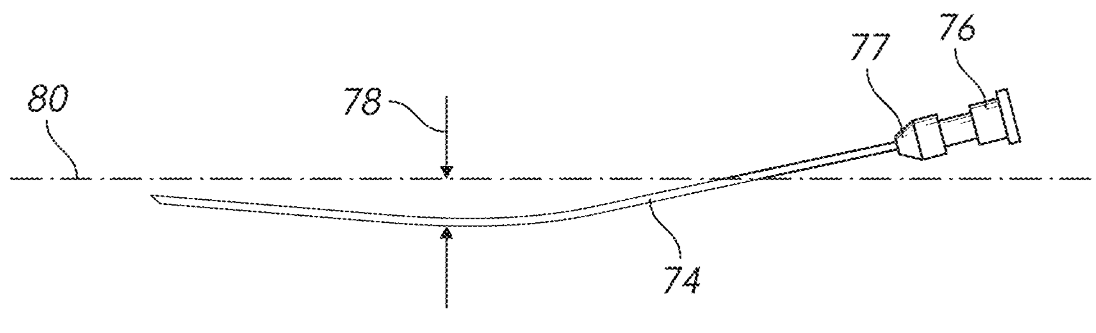
FIG. 11 is an elevation view, showing a bent needle used in the identification and isolation of a target nerve.

Step 6—A 22-gauge 3.5 inch spinal needle 74 (for normal body habitus, with 5.0 inch being used for larger body habitus) is bent into a deep arcuate shape similar to what is shown in FIG. 11. The bend introduces an offset 78 to the path of the needle, which allows the nerve to be cradled by the needle while creating a palpable location to assist the surgeon in locating the transection site. The physician provides an offset suitable for the depth of adipose tissue (subcutaneous fat) present in the particular patient. The amount of bend is selected so that the arcuate needle can pass beneath the targeted nerve site while stylet 76 remains outside the patient.

Figure 12:
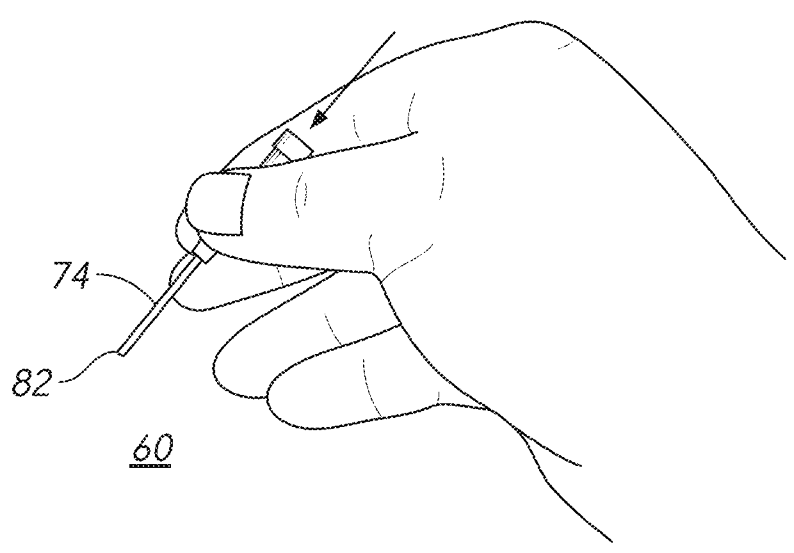
FIG. 12 is a perspective view, showing the insertion of a bent needle.
Figure 13:
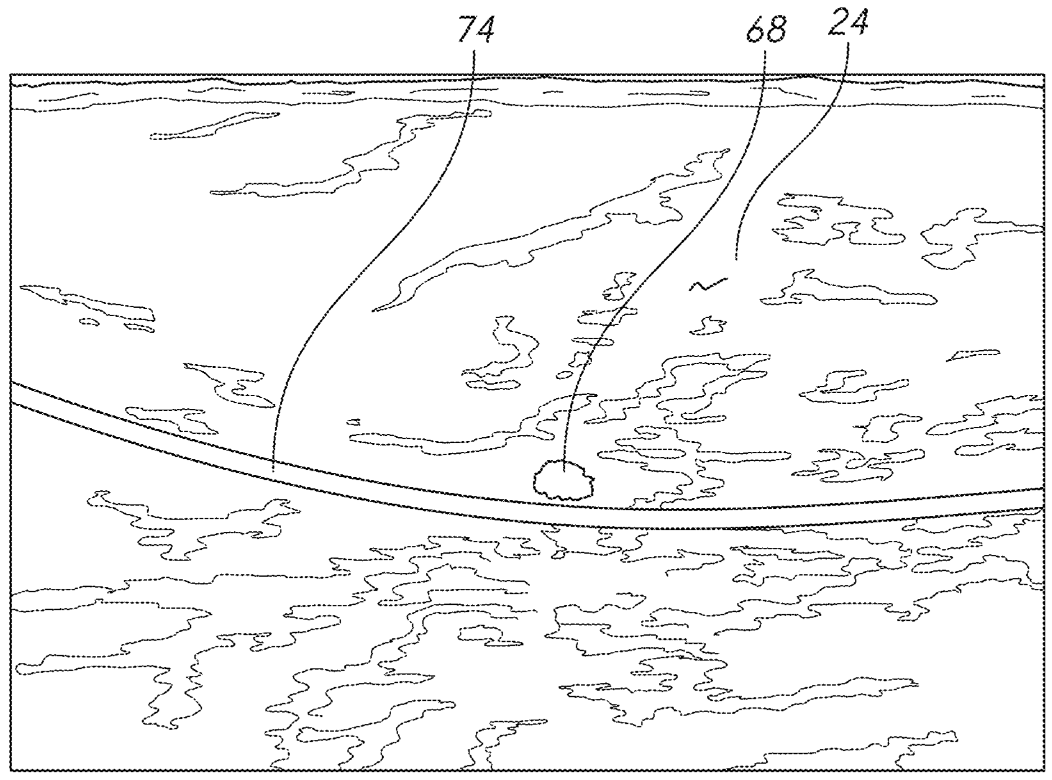
FIG. 13 is an ultrasound image, showing the placement of the bent needle of FIG. 12.

Step 7—As shown in FIG. 12, the physician inserts bent needle 74 through insertion point 82. Ultrasound is again used to guide the needle's advancing tip. FIG. 13 shows the ultrasound display as bent needle 74 advances beneath and past nerve 68. The needle hooks under the nerve and isolates it from other adjacent structures. The needle also serves as a physical barrier for the surgeon to confirm the correct nerve target (in addition to the presence of the methylene blue).

Step 8—A needle placement is performed for each target nerve location. A skin marker is then applied over the previously-created skin indentation so that the surgeon can see the correct location and angle for making small incisions over each site. The proximal end of the needle (stylet) can also be seen outside the skin as it is used as a visual guide for the surgeon to have the correct angle of approach/depth.

Figure 14:
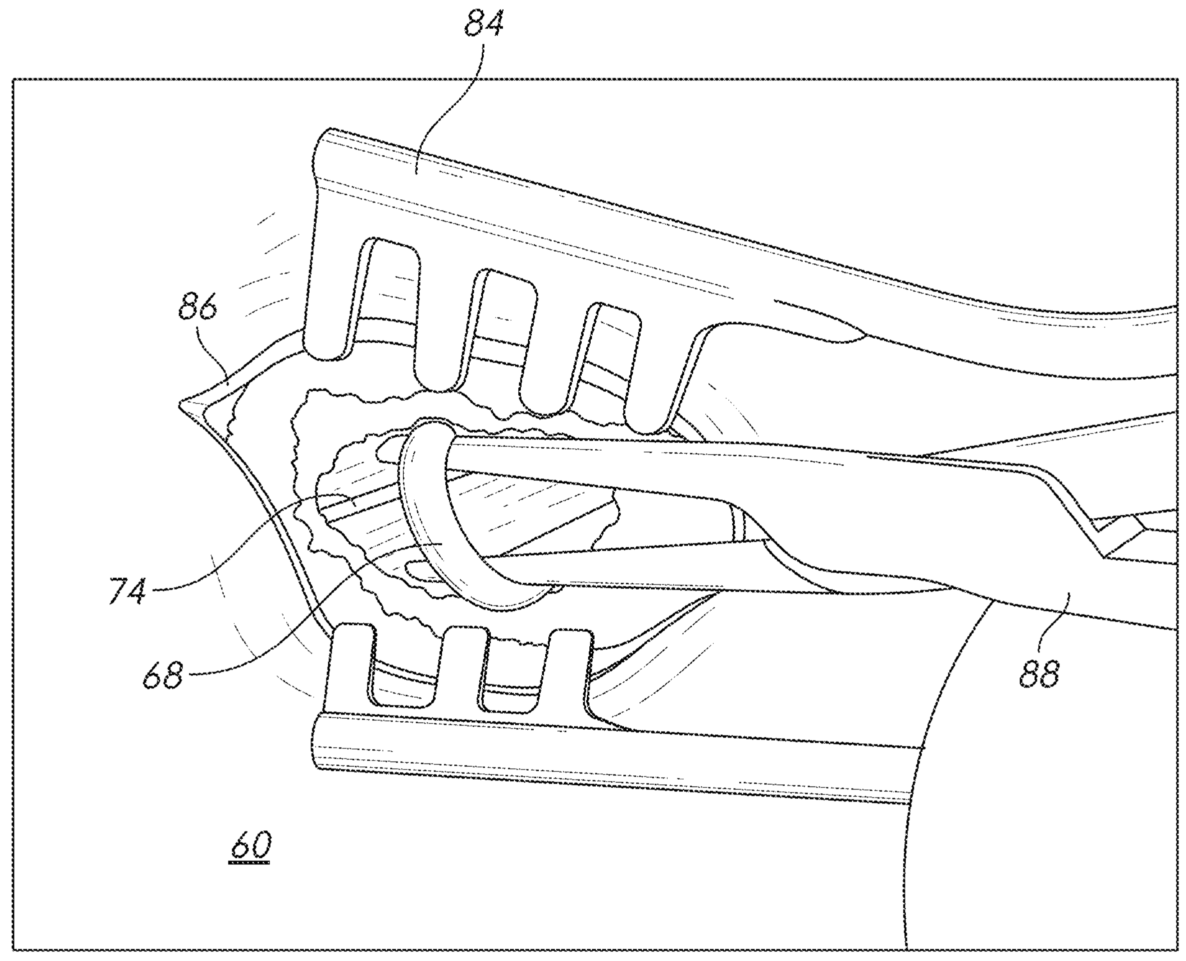
FIG. 14 is a perspective view, showing the isolation of a target nerve.
Figure 15:
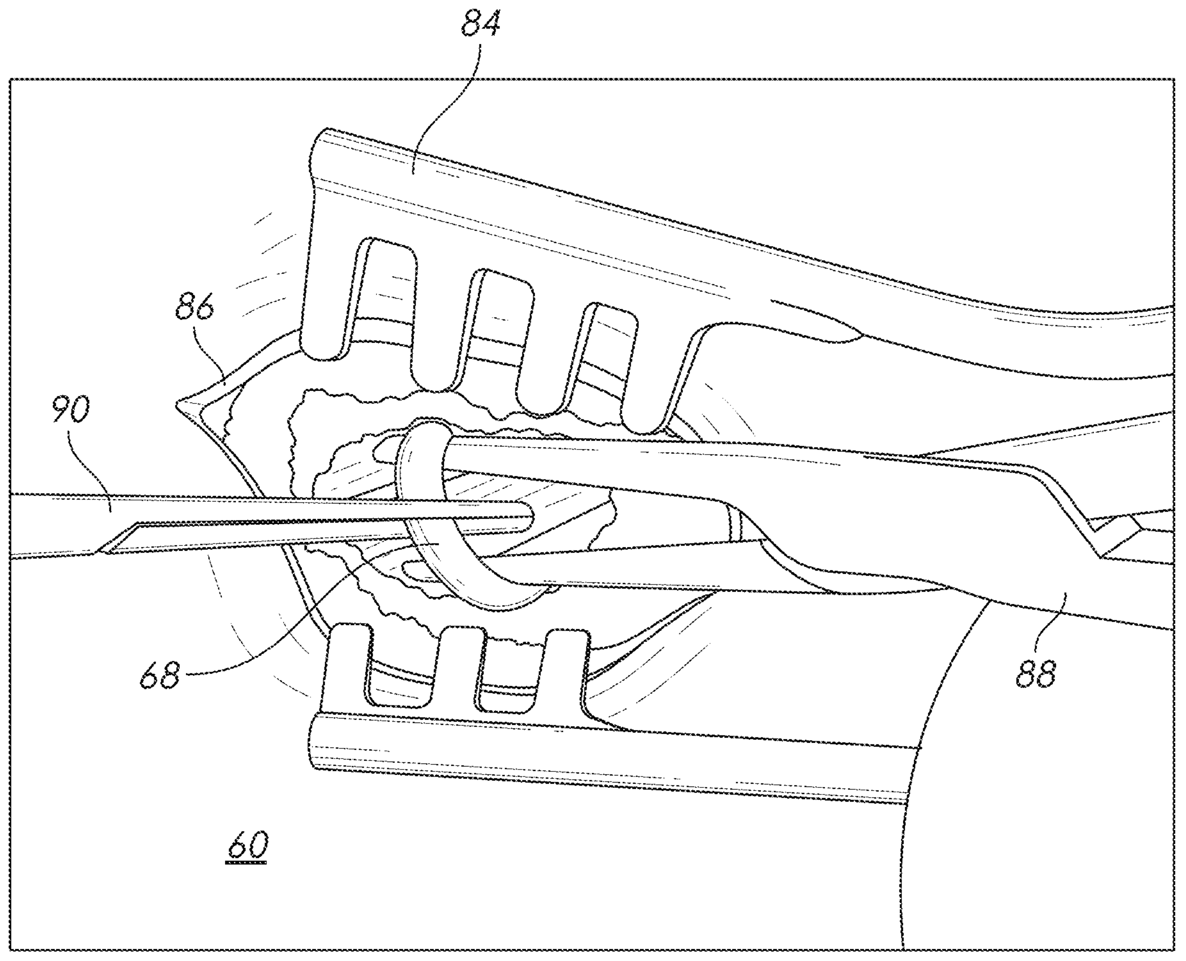
FIG. 15 is a perspective view, showing the transection of a target nerve.

Step 9—The skin proximate the incision sites is infiltrated with 1% lidocaine without epinephrine. FIG. 14 shows a target site after the surgeon has made a small incision 86. Dissection is carried out with monopolar electrocautery through the soft tissue. Metzenbaum scissors are used to spread tissue down to the needle and identify the target nerve. Dissection is continued down to the level where the blue dye is encountered. Self-retaining retractor 84 is applied to hold the site open. The reader will note how bent needle 74 lies beneath targeted nerve 68. At this point the surgeon will see the blue color of the exposed nerve—the result of the dying with methylene blue. The surgeon will also note the presence of bent needle 74 lying beneath the exposed nerve. These two indicators—the location of the needle and the presence of the dye-independently confirm for the surgeon that the correct nerve location has been identified. Right angle hemostat forceps 88 are initially applied with the jaws clamped together. The tip of the hemostat is passed under the nerve and the jaws are then carefully opened to isolate a small length of the nerve between the two jaws as shown in FIG. 14. In FIG. 15, Metzenbaum scissors 90 are used to transect the exposed portion of the target nerve 68. The Metzenbaum scissors are viewed from directly above at a time when the jaws are open and before the cut is made. One jaw lies above the nerve and one jaw lies below.

Figure 16:
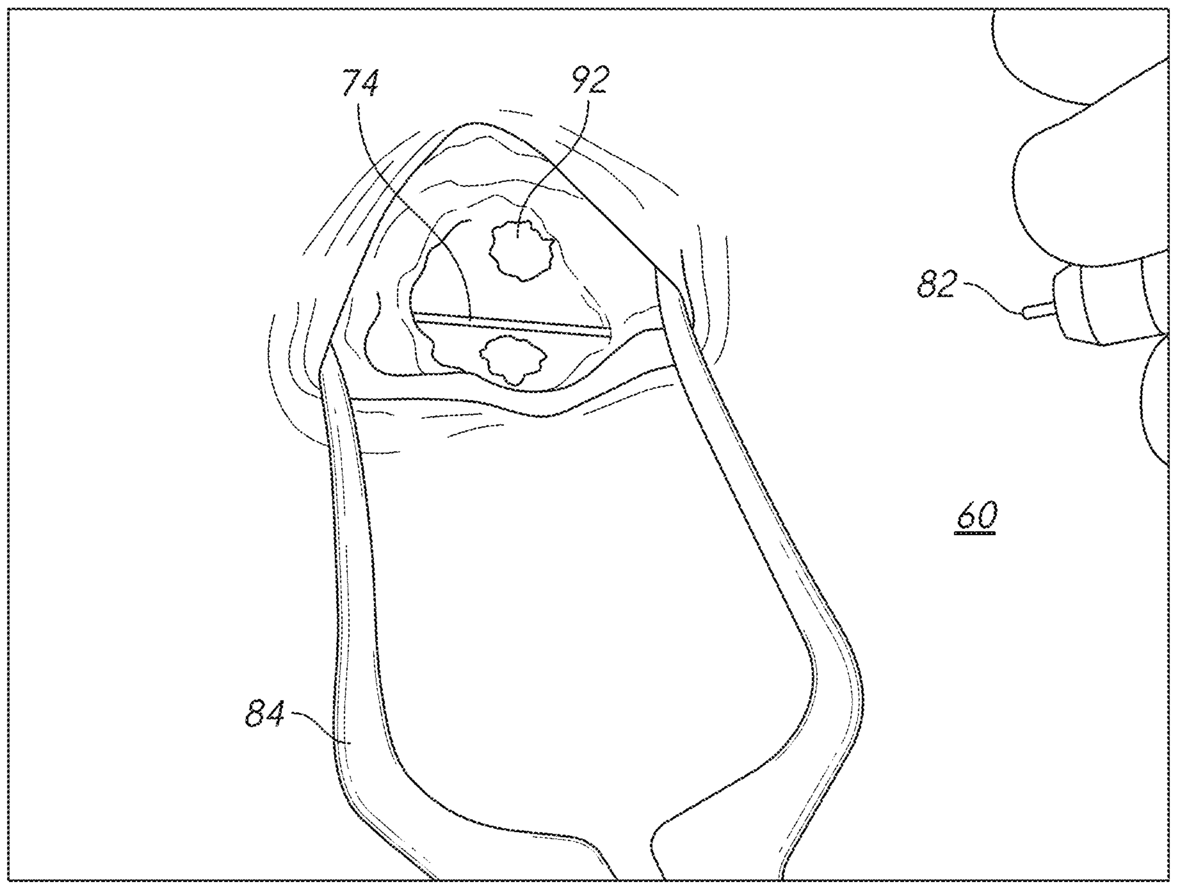
FIG. 16 is a perspective view, showing a target nerve after transection and before closure.

Step 10—FIG. 16 illustrates the confirmation step. The severed ends of transected nerve 92 are clearly visible on either side of bent needle 74. The blue dye remains within the transection section of nerve tissue-making the nerve tissue easy to visually distinguish from the surrounding tissue.

Following the confirmation step the bent needle is withdrawn. Bipolar electrocautery is used for hemostasis of any associated bleeding vessels running with the nerve while avoiding electrocautery to the proximal transected nerve if possible. The wound is irrigated and closed using conventional techniques.

The inventive method thus described has produced excellent results. Chronic knee pain has been eliminated for most patients. And—if pain persists—the invention does not impair the future ability to have total knee arthroscopy for those patients who want it. Of the approximately 70 patients treated using the inventive process, however, only two have gone on to have a total knee replacement. Most patients have experienced statistically significant pain reduction and functional improvement.

Although the preceding descriptions contain significant detail, they should not be construed as limiting the scope of the invention but rather as providing illustrations of the preferred embodiments of the invention. Those skilled in the art will know that many other variations are possible without departing from the scope of the invention. Accordingly, the scope of the invention should properly be determined with respect to the claims to follow rather than the examples given.

Having described our invention, we claim:

1. A method for relieving knee pain in a patient, comprising:

(a) using ultrasound imaging to locate an emergence position of a medial saphenous nerve of said patient through a sartorius muscle of said patient;

(b) using said ultrasound imaging to follow said medial saphenous nerve distally into a medial knee joint of said patient in order to identify additional branches that emerge from said sartorius muscle in a more inferior position;

(c) using said ultrasound imaging to locate a position of an infrapatellar saphenous nerve in said patient;

(d) based on said nerve identifications, determining proposed nerve transection sites selected to provide said knee pain relief;

(e) marking a location of each proposed nerve transection site using skin indentations;

(f) injecting an anesthetic into each of said proposed nerve transection sites;

(g) determining whether said anesthetic injections provide pain relief for said patient;

(h) where said pain relief is obtained, marking and transecting nerves within said proposed nerve transection sites by, (i) injecting a marking dye around each of said nerves in said proposed nerve transection sites, (ii) hooking a curved needle beneath each of said nerves within each of said proposed nerve transection sites in order to isolate said nerves from surrounding tissues, (iii) creating an incision proximate each of said proposed nerve transection sites and dissecting tissue to expose said nerves within each of said proposed nerve transection sites, (iv) identifying each of said nerves within said proposed nerve transection sites by inspecting for the presence of said dye and said curved needle, and (v) following said identification, transecting each of said nerves within said proposed nerve transection sites.

2. The method for relieving knee pain as recited in claim 1 wherein ultrasound imaging is used to guide an injection needle for said step of injecting an anesthetic into each of said proposed nerve transection sites.

3. The method for relieving knee pain as recited in claim 1 wherein ultrasound imaging is used to guide an injection needle for said step of injecting a marking dye around each of said nerves in said proposed nerve transection sites.

4. The method for relieving knee pain as recited in claim 1 wherein ultrasound imaging is used to guide said curved needle placed beneath each of said nerves.

5. The method for relieving knee pain as recited in claim 1 wherein said marking dye is methylene blue.

6. The method for relieving knee pain as recited in claim 1 further comprising:

(a) passing a set of hemostat jaws under a nerve to be transected;

(b) opening said set of hemostat jaws to isolate a small length of said nerve to be transected; and (c) transecting said nerve within said small length of said nerve.

7. The method for relieving knee pain as recited in claim 1, further comprising after each of said transections inspecting a first and second transected end of each of said transected nerves for a presence of said marking dye within said transected end.

8. A method for relieving knee pain in a patient, comprising:

(a) using ultrasound imaging to locate an emergence position of a medial saphenous nerve of said patient through a sartorius muscle of said patient;

(b) using said ultrasound imaging to follow said medial saphenous nerve distally into a medial knee joint of said patient in order to identify additional branches that emerge from said sartorius muscle in a more inferior position;

(c) using said ultrasound imaging to locate a position of an infrapatellar saphenous nerve in said patient;

(d) based on said nerve identifications, determining a proposed nerve transection site selected to provide said knee pain relief;

(e) injecting an anesthetic into said proposed nerve transection site;

(f) determining whether said anesthetic injection provided pain relief for said patient;

(g) where said pain relief is obtained, marking and transecting a nerve within said proposed nerve transection site by, (i) injecting a marking dye around said nerve in said proposed nerve transection site, (ii) hooking a curved needle beneath said nerve within said proposed nerve transection site in order to isolate said nerve from surrounding tissues, (iii) creating an incision proximate said proposed nerve transection site and dissecting tissue to expose said nerve within said proposed nerve transection site, (iv) identifying said nerves within said proposed nerve transection site by inspecting for the presence of said dye and said curved needle, and (v) following said identification, transecting said nerve within said proposed nerve transection site.

9. The method for relieving knee pain as recited in claim 8 wherein ultrasound imaging is used to guide an injection needle for said step of injecting an anesthetic into said proposed nerve transection site.

10. The method for relieving knee pain as recited in claim 8 wherein ultrasound imaging is used to guide an injection needle for said step of injecting a marking dye around said nerve in said proposed nerve transection site.

11. The method for relieving knee pain as recited in claim 8 wherein ultrasound imaging is used to guide said curved needle placed beneath said nerve.

12. The method for relieving knee pain as recited in claim 8 wherein said marking dye is methylene blue.

13. The method for relieving knee pain as recited in claim 8 further comprising:

(a) passing a set of hemostat jaws under said nerve to be transected;

(b) opening said set of hemostat jaws to isolate a small length of said nerve to be transected; and (c) transecting said nerve within said small length of said nerve.

14. The method for relieving knee pain as recited in claim 8, further comprising after said transection inspecting a first and second transected end of said transected nerve for a presence of said marking dye within said transected end.

15. A method for relieving knee pain in a patient, comprising:

(a) using ultrasound imaging to locate an emergence position of a medial saphenous nerve of said patient through a sartorius muscle of said patient;

(b) using said ultrasound imaging to follow said medial saphenous nerve distally into a medial knee joint of said patient in order to identify additional branches that emerge from said sartorius muscle in a more inferior position;

(c) using said ultrasound imaging to locate a position of an infrapatellar saphenous nerve in said patient;

(d) based on said nerve identifications, determining a proposed nerve transection site selected to provide said knee pain relief;

(e) injecting an anesthetic into said proposed nerve transection site;

(f) determining whether said anesthetic injection provided pain relief for said patient;

(g) creating a record of a nerve distribution found in said patient and a location of said proposed nerve transection site;

(h) where said pain relief is obtained, marking and transecting a nerve within said proposed nerve transection site by, (i) using said previously created record to locate said proposed nerve transection site, (ii) injecting a marking dye around said nerve in said proposed nerve transection site, (iii) hooking a curved needle beneath said nerve within said proposed nerve transection site in order to isolate said nerve from surrounding tissues, (iv) creating an incision proximate said proposed nerve transection site and dissecting tissue to expose said nerve within said proposed nerve transection site, (v) identifying said nerves within said proposed nerve transection site by inspecting for the presence of said dye and said curved needle, and (vi) following said identification, transecting said nerve within said proposed nerve transection site.

16. The method for relieving knee pain as recited in claim 15 wherein ultrasound imaging is used to guide an injection needle for said step of injecting an anesthetic into said proposed nerve transection site.

17. The method for relieving knee pain as recited in claim 15 wherein ultrasound imaging is used to guide an injection needle for said step of injecting a marking dye around said nerve in said proposed nerve transection site.

18. The method for relieving knee pain as recited in claim 15 wherein ultrasound imaging is used to guide said curved needle placed beneath said nerve.

19. The method for relieving knee pain as recited in claim 15 wherein said marking dye is methylene blue.

20. The method for relieving knee pain as recited in claim 15 further comprising:

(a) passing a set of hemostat jaws under said nerve to be transected;

(b) opening said set of hemostat jaws to isolate a small length of said nerve to be transected; and (c) transecting said nerve within said small length of said nerve.

* * * * *